United States Patent [19]
Zucchetti et al.

[11] Patent Number: 6,037,481
[45] Date of Patent: Mar. 14, 2000

[54] PROCESS FOR STABILIZING LEVOGYRE ASCORBIC ACID (LAA), A STABLE AQUEOUS LAA COMPOSITION, A PROCESS FOR PREPARING A STABLE TOPICAL SOLUTION, AN EMULSION, A VITAMIN PRODUCT, AND A METHOD FOR COSMETIC, PHARMACEUTICAL OR NUTRITIONAL TREATMENT

[75] Inventors: Roberto Alcantara Martins Zucchetti; Simoni Chitarra Souza; Philippe Joseph Pommez; Karla De Souza Araújo, all of São Paulo, Brazil

[73] Assignee: Industria E Comércio De Cosmeticos Natura Ltda, São Paolo, Brazil

[21] Appl. No.: 08/955,524

[22] Filed: Oct. 22, 1997

[30] Foreign Application Priority Data

Aug. 8, 1997 [BR] Brazil ...................................... 9704418
Sep. 16, 1997 [BR] Brazil ...................................... 9704728

[51] Int. Cl.$^7$ .................................................. C07D 307/02
[52] U.S. Cl. ............................. 549/315; 514/474; 424/59
[58] Field of Search ........................... 514/474; 549/315; 424/59

[56] References Cited

U.S. PATENT DOCUMENTS 2,132,662  10/1938  Volwiler et al. ........................ 260/501
2,721,161  10/1955  Maiese ...................................... 167/81
4,983,382   1/1991  Wilmert et al. ........................... 424/62
5,140,053   8/1992  Darr et al. .............................. 514/474

OTHER PUBLICATIONS

WO 98/00102 WIPO, published Jan. 8, 1998.
WO 98/00103 WIPO, published Jan 8, 1998.

*Primary Examiner*—Amelia Owens
*Attorney, Agent, or Firm*—Smith, Gambrell & Russell, LLP

[57] ABSTRACT

The present invention refers to a process for stabilizing LAA in an aqueous medium, which includes the step of contacting the LAA with at least one compound capable of forming hydrogen bridges with the LAA. In another aspect, the invention relates to a stable aqueous LAA composition which includes, in addition to said ascorbic acid, at least one compound which is linked to the LAA by hydrogen bridges, and to a process for preparing it. The present invention further relates to an emulsion including, in its aqueous phase, at least one compound linked to levogyre ascorbic acid (LAA) by hydrogen bridges. Further according to the present invention a vitamin product is provided, in which a stable LAA composition as described above is contained in organic envelopes which enable a gradual and prolonged release of the LAA into the organism. The vitamin product may further include a compound capable of stimulating the metabolism of the fibroblasts. The present invention further relates to a method for cosmetic, therapeutical or nutritional treatment, which includes the administration of a composition as described above.

57 Claims, 5 Drawing Sheets

PROCESS FOR STABILIZING LEVOGYRE ASCORBIC ACID (LAA), A STABLE AQUEOUS LAA COMPOSITION, A PROCESS FOR PREPARING A STABLE TOPICAL SOLUTION, AN EMULSION, A VITAMIN PRODUCT, AND A METHOD FOR COSMETIC, PHARMACEUTICAL OR NUTRITIONAL TREATMENT

FIELD OF THE INVENTION

The present invention refers to a process of stabilizing levogyre ascorbic acid, also known as LAA or, more popularly, "Vitamin C", and to cosmetic, pharmaceutical or nutritional stable aqueous—or water-containing—compositions containing LAA.

BACKGROUND OF THE INVENTION

The levogyre ascorbic acid, hereinafter called LAA, presents the following formula:

and is an element known since long ago in the pharmacopeia, in medicine and in the cosmetic industry. Its application aims at the most varied benefits, from the treatment of stomachal problems, regeneration of skin signs hygienization and attenuation of skin marks. The expression "skin signs" as used herein means the signs of skin aging, such as wrinkles resulting from the action of time and from external factors such as climatic actions (sunshine, wind and temperature).

Examples of the employ of LAA in medicine are described in U.S. Pat. No. 2,132,662, granted in November, 1938 to Abbott Laboratories, the inventors of which are Ernst H. Volwiler and others, in this case as an antiscorbutic agent, and in U.S. Pat. No. 2,721,161, granted in 1955 to the inventor Maise and others, who taught the use of LAA plus a non-ionic surfactant in preparing oral or intravascular compositions for restoring the level of LAA in the blood.

The same is true of the cosmetic industry, where the LAA in molecular form, either associated or not with its salts and esters, has been employed in fighting the cutaneous aging process. In large part, in the segment of cosmetics, the salts and esters of the LAA alone are employed more frequently than the LAA in its molecular form, since the former are chemically more stable, which has been resulting in less effective products than the case would have been if the LAA in its molecular form had been used.

As to the form of action intended by the cosmetics industry for fighting cutaneous aging, be it by using the LAA or its derivatives, studies carried out by the applicant and the literature show that skin aging comprises a regressive phase of the life cycle with anatomic and physiological alterations, with degradation of certain organs and tissues.

Some literature references which incorporate the studies made by the applicant include: 1- DARR, D.; COMBS, S.; PINNELL, S. Ascorbic acid and collagen synthesis: Rethinking a role for lipid peroxidation. *Archives of Biochemistry and Biophysics*. 307, 331–5, 1993; 2- PINNEL, S. ; MURAD, S. Vitamin C and collagen metabolism. In: KLIGMAN, A. M.; TAKASE, Y., Cutaneous aging Du University Medical Cancer, 275–92, 1988; 3- PINNELL S. Vitamina C tópica (Topical Vitamin C). *Revista de Cosmiatria & Medicina Estética*. 31–6, 4o. trim 1995; 4- DARR, D.; COMBS, S.; DUNSTON, S.; MANNING, T.; PINNEL, S. Topical Vitamin C protects porcine skin from ultraviolet radiation-induced damage. *British Journal of Dermatology*. 127, 247–53, 1992; 5- PINNELL, S. Regulation of collagen biosynthesis by ascorbic acid: a review. *The Yale Journal of Biology and Medicine*, 58, 553–9, 1985.

The aging manifests itself on the skin by the loss of elasticity, loss of turgency, formation of wrinkles and the appearance of stains. Among the physiological alterations which actively contribute to this process, we can mention decrease in immunological functions, decline of basal metabolism, alterations in the structure of the conjunctive tissue, decrease in the capability of renewing the cutaneous lipids and in the hygroscopic components, leading to a lesser power of hydric retention and, consequently, to dehydration of the skin.

All of these alterations are the reflex of a series of internal and external factors which jointly contribute to the aging process.

As internal factors, directly controlled by the genetic patterns of the individual, the following can be cited: the chronological factor, defined by the aging, influenced by the genetic information contained in the cells; the immunological factor, given by the decrease of the Langerhans cells, responsible for the immunity vigilance of the skin; the hormonal factor, given by the decrease of the hormonal activity, especially of androgenic hormones, impairing the capability of hydric retention of the epidermis.

Interacting with the internal factors, a series of external factors too modulate the cutaneous aging, such as the photoaging, caused by the UV-A and UV-B radiations. The ultraviolet radiation acts at intercellular levels, inducing alterations in the DNA capable of forming incorrect proteins and enzymes, accelerating and altering the activities of cells. At the extracellular level, it may cause structural alterations in the collagen and elastin fibers and in the proteoglycans, which are fundamental in maintaining the turgor and the structure of the dermic layer. These alterations form groups of amorphous mass, which cause a lowering in the outer surface of the skin, also known as wrinkles. In addition to these damages, the UV radiation also promotes reactions of the molecular oxygen with lipids and proteins of the cellular membranes (lipoperoxidation), forming free radicals, which are molecules extremely dangerous to the cells.

In addition, one can point out as external factors the so-called Environmental Factors, for example, excessively low or high temperatures, wind, low relative moisture of the air and pollution, which in turn attack the protecting hydrolipidic mantle, leading to the loss of transepidermal, water with the consequent dehydration of the skin. There are equally the Emotional Factors and the Living Habits, generally stressing in the big cities and characterized by poor alimentation, smoking and drinking, which cause either alterations or unbalances in the metabolism of the lipids and proteins of the dermic layer.

These factors affect the skin in some way and can be enhanced by the age of the individual or by the biological cycle.

The biological cycles of an individual are constituted by a set of alterations resulting from these external and internal factors already described. The way in which each cycle has been lived by the individual will result in the degree of alterations.

The cutaneous aging can be divided into 3 main cycles: the first one begins at the age of 30, the second one comprises the range from 45 to 60 years of age, and the third one from the age of 60 on.

In the age group of from 30 to 45 the skin, in general, does not present any visible marks. The action of the free radicals decreases the activity of cells involved in the immunological responses. Every 10 years the skin loses 10% of this defence mechanism. Collagen and elastin, damaged by the UV radiation, have their restoration decreased. Natural aging and the action of free radicals are also responsible for this reduction.

Between 45 and 60 years of age, there is a drop in the production of tallow by the sebaceous glands, due to the lesser concentration of androgenic hormones. The signs of weakening of the circulatory system become more evident. The damages caused by free radicals intensify and the deficiencies of the immune system become more accented, in addition to a decrease in efficiency of the fibroblasts, impairing the restoration of collagen. There is also a reduction in the production of elastic fibers and of glucosaminoglycans, leading to the loss of sustainment.

From 60 years of age on, the signs which began in the preceding cycle become more accented. The sebaceous glands are virtually destroyed, because they receive less androgenic stimulus and the deficient circulatory picture becomes accented, thus decreasing the nutritional contribution and the elimination of toxins. An increase in the immunologic deficiency is noted, especially in the areas which are exposed to UV radiation, and the wrinkles become accented with an increase in seriousness of the previously described picture, due to the drop in production of collagen, elastin and glucosaminoglycans.

The technologies for treatment of the skin have tried to treat not only the visible signs of aging, but also to actuate more and more deeply on the causes thereof, by preventing potential risks which might contribute to the aging process. On this basis, the active principles are developed for actuating at specific sites of action, acting directly where they are required, that is to say, in deeper layers of the skin and directly on the aspects which guarantee the cutaneous sustainment.

The LAA has been one of the most researched elements for this purpose, the main focus being the obtention of its stabilization, since it is one of the main antioxidants existing in our blood and in other fluids of the tissues.

Just as the body, the skin too grows old. Many of the unwanted effects of the cutaneous aging (such as wrinkles) can be attributed to the loss of connective tissue. With the aging the dermis becomes thinner and over 20% of its thickness is lost.

The LAA plays a vital role in the growth and repair of connective tissue. Many studies have proven its action in the process of cellular regeneration and skin protection, by a series of mechanisms. The LAA is directly involved in the stimulation of the biosynthesis of collagen, a macromolecule that is fundamental for maintaining the tonus of the skin. As an antioxidant substance, it fights directly the free radicals, which are elements connected with the cutaneous aging (an action proved by studies "in vitro"). Besides, the LAA is capable of protecting the skin against UV radiation and its subsequent damages.

Scientific reports show that the skin, especially with the aging, becomes deficient in LAA.

The amount of LAA supplied by the alimentation is not sufficient to actuate on the skin effectively and to fight the damages of the aging process. The LAA, via ingestion of food or by oral supplementation, is distributed throughout the organism and, depending on the needs of the latter, may not reach the skin in quantities sufficient to stimulate the synthesis of collagen, and to fight free radicals. In this way, under limit conditions of ascorbic acid, the latter can be absorbed and used preferably to maintain the more vital needs of the organism, to the detriment of the supply in the cutaneous tissue.

Higher levels of LAA in the skin cannot be obtained orally alone. Studies with topical applications of LAA indicate that it reaches pharmacological levels much higher than those found in normal skin. In this way, by topical use, it is possible to reach ideal concentrations of LAA, so that it can act efficiently and directly as an antioxidant, antiphologistic and regenerative agent.

Collagen, the most abundant protein of the skin and fundamental for maintaining the tonus of the skin, is regulated in every step of its synthesis.

The LAA is essential in the biosynthesis of collagen, actuating as an important cofactor of its fundamental enzymes: prolylhydroxylase and lysylhydroxylase, which actuate converting proline into hydroxyproline (an aminoacid that is fundamental to the stability of the triple helix of procollagen) and in converting lysin into hydroxylysin (another aminoacid that is fundamental to the stabilization of the structure of collagen, participating in the formation of intermolecular links and imparting mechanical stability to the fiber).

Independently of its participation in the hydroxylation of lysin and proline, the LAA can have an additional effect on the biosynthesis of collagen by genetic regulation, promoting an inducing effect in the synthesis of collagen upon stimulating the genic transcription for collagens of type I and type III. Studies "in vitro" with human fibroblasts show an increase in the synthesis of mRNA of 2 to 3 times as high, when in the presence of LAA. These mRNA also prove to be about 2 times as efficient in the translation of the polypeptidic chains of collagen, without causing any alteration in the process of synthesis of non-collagenic proteins.

There is also the action of the LAA on the production of glucosaminoglycines, components of the extracellular matrix of the dermis, closely related to the collagen fibers. In the presence of LAA, their synthesis can be increased from 30 to 90%, with 50% of increase in their deposition in the extracellular matrix.

The LAA is also one of the main biological antioxidants, by virtue of its reducing properties, being capable of neutralizing these highly reactive species, important figures in the aging process. It can also act an antioxidant in the peroxidative processes of metabolization of fats and formation of free radicals, besides contributing to maintain vitamin E in the organism, also an important antioxidant, in its reduced form, assisting in the protection against lipoperoxidation and, consequently, avoiding injury to the cellular membranes. It should be stressed that qualitatively, the antiradical action of the LAA is superior to that of Vitamin E and Glutation, even if associated.

The damages to the skin produced by ultraviolet radiation are due, in part, to the generation of certain varieties of reactive oxygen, as the superoxide anion, the singlet oxygen and the hydroxyl radical. The oxidative aggression promoted by the radication with generation of free radicals results in generalized damages to the constituents of the skin.

As a result of exposition to the sunshine, the dermis undergoes major alterations, accenting the normal process of cutaneous aging. In this case, we have the degeneration of the elastic material, degeneration of the collagen and accumulation of glucosaminoglycans. The fibroblasts, exposed to UV radiation, reduce or even lose their capacity of synthesis of macromolecules of sustainment.

The LAA in topical use is capable of protecting the skin against UVA and UVB radiations. However, it does not actuate as a sun filter, since it is not capable of absorbing radiation in this spectrum. Its protecting effect is directly connected to its antiradical action. Its role as an antioxidant is essential to protect the skin against oxidative damages produced by exposition to radiation and to the inflammatory reaction associated thereto.

The LAA cannot be synthesized by the human body, but it is available in vegetables and mainly in citric fruits. Pure LAA, either extracted from fruits or chemically synthesized, is a white or slightly yellowish powder, which has a relative stability when dissolved in an aqueous medium. This compound is easily oxidable in the presence of atmospheric air, changing into dehydro ascorbic acid, in addition to other products resulting from the oxidation. Such a transformation decreases its physiological properties, principally in the use conditions in which there is exposition of the compound to atmospheric air, as for instance, when using a topical solution.

In a simplified way, the instability of LAA manifests itself by the fact that, when dissolved in an aqueous medium, it becomes ionized, forming LAA anions and releasing H+ ions.

Due to this instability, although it shows greater efficiency when in its original form, that is to say, in its molecular formula, the LAA is used in the form of its salts or esters, so that the resulting compositions have greater stability for long periods of time, thus preventing degradation due to contact with the oxygen dissolved in water and absorbed from atmospheric air.

However, many works have been carried out for the main purpose of achieving stability of the LAA in its molecular form, in order to enable its use in medicaments and cosmetic compositions. An example of this approach can be found in U.S. Pat. No. 4,983,382 of Jan. 8, 1991. According to this patent, a solution containing LAA would become stable by its being added to an organic solution comprising a first co-solvent, water up to 12% by weight and a second co-solvent in a concentration of up to 90%, based on the total weight of the solution and further containing, compulsorily, ethanol in a concentration of at least 40% by weight of the solution.

The disadvantage of this type of organic solution for the cosmetic and pharmaceutical industry or food industry consists in the fact, even though it can exhibit an acceptable stability of the LAA, the addition of ethanol in the mentioned contents causes the skin to become irritated and very dry, which may render the permeation of the LAA by corneous extract difficult, besides, of course, causing an unpleasant feeling to the user.

Another use of the LAA in its molecular form is described in Brazilian patent application PI 9008018, filed in the name of Bioderm, Inc. This document refers to a composition for reducing the depth or intensity of fine wrinkles on a skin affected by intrinsic or photoinduced aging. Although it does not make detailed comments about the stability of the LAA, the referred-to patent application describes a series of actions that are beneficial in the reduction of the depth or intensity of fine wrinkles by the use of a topical formulation which comprises, in combination with the LAA, tyrosine and a zinc salt such as zinc sulphate, and can be formulated either as a salve or as a hydrophilic cream. The compulsory inclusion of tyrosine and a zinc salt makes the solution more expensive for the consumer, because of the great number of ingredients for its production, and its effective action in fighting the cutaneous aging has not been totally proved yet.

In more recent works for achieving stability of the LAA in its molecular form, the objective was to avoid the degradation of the acid by maintaining the pH at low levels. In these works the appearance of ascorbates to the detriment of the maintenance of molecular LAA in the solution was credited to the occurrence of ionization of the LAA and its degradation due to the contact of the LAA-anion with oxygen (either atmospheric air or pure oxygen present in the solution).

In fact, the ionization of the LAA causes the formation of an ascorbate (LAA−), which is a metastable structure in water due to the electronic resonance between the carbons 1, 2, and 3 of the LAA, and the release of H+ ions.

This reaction is governed by the spontaneousness (free energy or "DeltaG<0") of the LAA for ionizing until a dynamic balance between the reactants (LAA) and the products (LAA−+H+) is reached, and it can be represented as follows:

$$LAA \leftrightarrow LAA- + H+.$$

In order for the minimum amount of ascorbate to be formed as a product of ionization and, therefore, for the maximum of LAA to remain stable, it was believed that the pH of the solution should be as low as possible. For this purpose, the practice common to various earlier solutions was to add any acid whatever as a citric acid, for instance, or to increase the initial concentration of LAA.

The pH of such a solution containing LAA was related to the concentration of LAA by the following equation:

$$pH = pK_1 + \log((LAA)/(LAA-))$$

wherein pH indicates the degree of acidity of the solution; $pK_1$ is the first constant of ionization of the LAA, equal to 4.2; (LAA) is the concentration of LAA in its molecular form, contained in the solution; and (LAA−) is the concentration of ascorbate contained in the solution.

Figure 1:
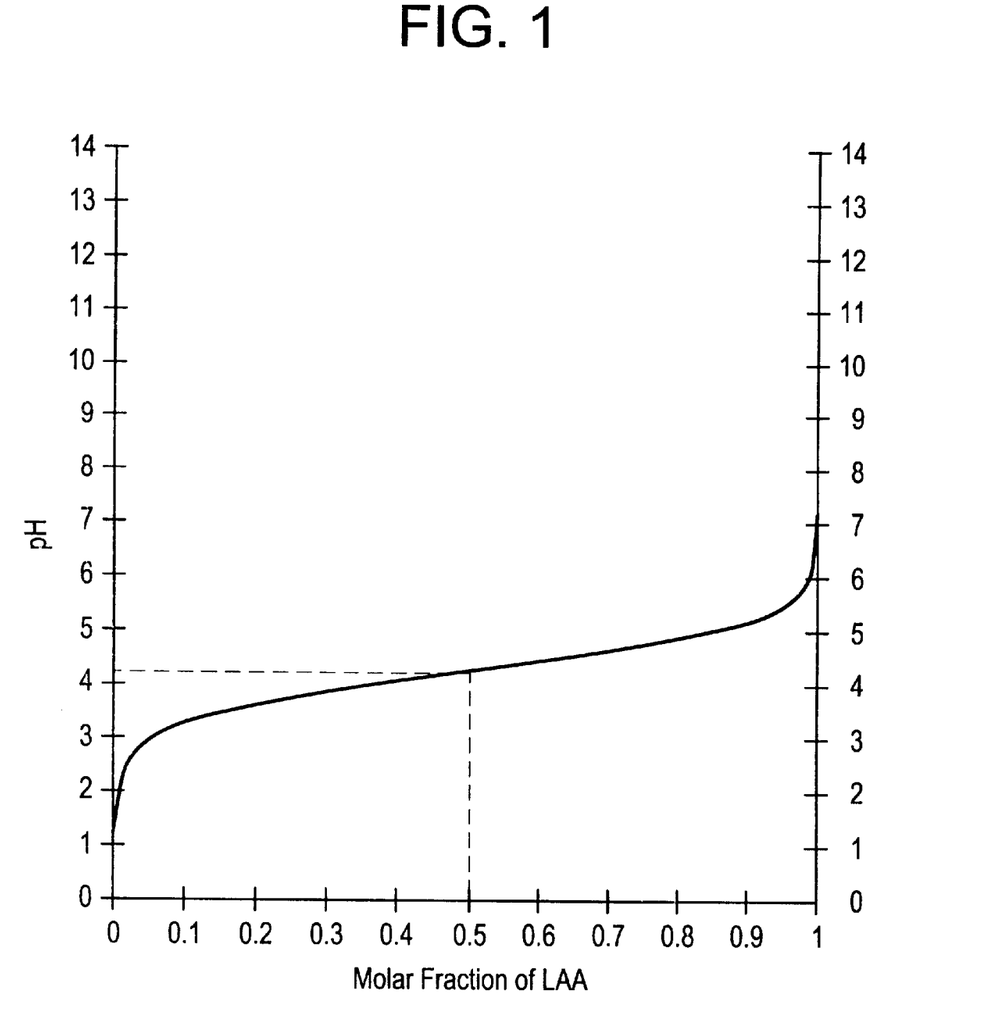
FIG. 1 represents a pH curve versus the molar fraction of LAA−. In this figure, one can see that high concentrations of LAA and low concentrations of LAA− correspond to low pH values.

Thus, by the above equation, read according to the knowledge from the prior art, in order for the biggest possible amount of LAA not to ionize (higher stability), the pH value of the solution should be lower than the $pK_1$, a fact which has probably guided most of the solutions known from the prior art. Graphically, this statement can be confirmed by analyzing FIG. 1, which represents a curve of pH versus the molar fraction of the LAA−. In this figure, we can see that for low pH values, we would have high concentrations of LAA and low concentrations of LAA−.

U.S. Pat. No. 5,140,043, granted on Aug. 8, 1992, for instance, teaches that the stabilization of the LAA in amounts higher than 1% by volume of water can be achieved in an aqueous medium, when a carrier for topical application in a water carrier ratio of at least 1:1 is associated to the LAA, the pH of the solution being lower than 3.5. Although this is a mutual association between the LAA contents, the relationship between water and the carrier and a low pH (lower than 3.5), the inventors give a great importance to the pH value in the stability of the LAA, the latter being considered an element guaranteeing that at least 82% of the LAA will remain in its non-modified molecular form, as can be seen from the passage of column 4, lines 7–9, of that document.

One of the disadvantages that are widely discussed by the inventors of that patent is the fact that the carbons 2 and 3 contain acidic hydrogens that are ionizable in water, by virtue of a physical and chemical characteristic of the LAA, that is to say, its ionization constant (pK) equal to 4.2.

In spite of the technical advance provided by that patent, the topical use of a solution as described therein can irritate the more sensitive parts of the skin, such as the contours of the eyes, for example. Since the pH of the human skin is about 4 to 5, this feeling of irritation may be easily attributed to what those inventors considered in the patent to be the "important factor guaranteeing stabilization of the LAA in its molecular form", that is to say, the low pH value of the solution, which is lower than 3.5, preferably lower than 2.5.

In addition, another great disadvantage of the solution disclosed in U.S. Pat. No. 5,140,043 is that, although the stability tests discussed therein are exhaustive, they took into account conditions that are far from the reality of the use of a product intended for topical application and for being handled for a long time. As regards the time of carrying out the test, it took only 12 weeks (84 days) and the low temperatures and luminosity to which the topical solution was exposed are hardly encountered in the home of a consumer or even in a doctor's office. With good chance, the conditions established for those tests would safeguard the topical solution only against the most severe actions of instabilization and degradation of the LAA.

More recently, the publication of patent application EP 670157, filed in the name of L'Oreal, describes the formation of a topical emulsion comprising an aqueous phase dispersed in an oily phase with the help of an emulsifier, dimeticonecopolyol, containing LAA at acidic pH of 3.5, at most. Just as in the case of U.S. Pat. No. 5,140,043, the emulsion described in the referred-to European patent application shows a profile that irritating the skin due to the low pH, which is enhanced by the compulsory inclusion of an artificial emulsifier, which in turn is also irritating.

Therefore, it is an objective of the present invention to provide an effective process for stabilizing LAA in an aqueous medium, which will enable the use of LAA in its molecular form, particularly in cosmetic, pharmaceutical or nutritional aqueous compositions which are stable enough to guarantee the results desired in storing and handling these compositions during cosmetic or therapeutical treatments, without causing damages to the organism of the individuals subjected to these treatments.

SUMMARY OF THE INVENTION

In a first principal aspect, the present invention refers to a process for stabilizing levogyre ascorbic acid (LAA) in a medium containing water, characterized by comprising the step of contacting the LAA with at least one compound capable of forming hydrogen bridges with the LAA.

In another principal aspect, the invention relates to a stable LAA composition in a medium containing water, which further comprises at least one compound which is linked to the LAA by hydrogen bridges.

Further according to the present invention, a vitamin product is provided, in which a stable LAA composition as described above is contained in organic envelopes which enable gradual and prolonged release of the referred-to LAA to the organism. This invention also relates to a vitamin product characterized by comprising a stable LAA composition as described above, inserted into an organic envelope, and by comprising, additionally, at least one compound capable of stimulating the metabolism of the fibroblasts.

The present invention further relates to an emulsion characterized by including, in its gaseous phase, at least one compound linked to levogyre ascorbic acid (LAA) by hydrogen bridges.

Also according to the present invention, a process is provided for preparing a stable LAA solution, characterized by comprising the steps of:

heating an amount of water;

adding to this amount of heated water a compound capable of forming hydrogen bridges with LAA in an amount ranging from 1 to 5% m/v, and the amount of heated water should be at a temperature capable of promoting dissolution of the compound that forms hydrogen bridges, besides simultaneously guaranteeing substantial elimination of any oxygen present;

homogenizing the product obtained in (b);

cooling the resulting product down to a temperature in the range of 10° to 40°;

adding to the mixture obtained in (d) from 5% to 20% m/v of LAA; and homogenizing the resulting solution.

The present invention further provides a method for the cosmetic, therapeutical or nutritional treatment, based on LAA, of an individual in need of such a treatment, which comprises incorporating LAA into the organism of said individual by administration of a stable LAA composition comprising, in addition to the ascorbic acid, at least one compound that is linked to the LAA by hydrogen bridges.

DETAILED DESCRIPTION OF THE INVENTION

After detailed studies, the present inventors found that the physical and chemical interaction of hydrogen bridges formed with at least one of the hydroxyl and carboxyl groups of the LAA enables the prolonged stabilization of this compound, even in aqueous compositions of frequent use, maintaining preserved all the beneficial characteristics of the compound when employed for cosmetic, pharmaceutical or nutritional purposes. The substantially physical and chemical interaction of the LAA with a compound that forms hydrogen bridges eliminates or at least decreases significantly the ionization reaction and, consequently, the degradation of the LAA. The interaction of the compound that forms hydrogen bridges avoids the formation of LAA− ions, thus guaranteeing the maintenance of the LAA in its molecular form.

The expression "a compound capable of forming hydrogen bridges" as used herein is intended to include any chemical compound which, when present in an aqueous medium together with LAA, interacts substantially in a physical and chemical way with the latter, therefore, without altering its original molecular form. This physical and chemical interaction can be represented by the scheme given below formed. "Linking power" is the value in Kcal/mol which defines the occurrence or non-occurrence of a hydrogen bridge, and for it to be defined as such a bridge, the link should exhibit about 4.5 to 5.5 Kcal/mol, preferably around 5 Kcal/mol.

An example of a compound useful to the present invention is a polymer comprising a plurality of equal monomer units with molecular weight less than 100 g/mol and with a heteroatomic group in an amount higher than about 70% of the ratio between the molecular mass of the polymer and the molecular weight of its monomer unit. The referred-to heteroatomic groups of the monomer units of the polymer described above are preferably hydroxyl (OH) or sulfidric (SH) groups, and the molecular weight of each monomer unit is preferably less than or equal to 60 g/mol.

For polymers with molecular masses on the order of less than from 70,000 g/mol to 200,000 g/mol, it is preferable that the amount of heteroatomic groups be about at least 0.9 of the ratio between the molecular mass of the polymer and the molecular weight of its monomer unit. For instance, for polymers with molecular mass lower than 70,000 g/mol, it is preferable that the amount of heteroatomic groups be wherein UM means the monomer unit of a generic compound. For the purposes of the present invention, one has found that, in a general way, any compound compatible with LAA and capable of forming the referred-to hydrogen bridges can be employed to promote an appropriate stabilization thereof. However, according to a preferred embodiment of the invention, one has deemed it appropriate to use polymers carrying a small monomer unit with great compatibility and low molecular weight, which leave a great amount of groups capable of interacting physically and chemically with at least one of the OH groups of carbons 2 or 3 and carboxyl (c=0) of carbon 1 of the LAA, and thus effecting the referred-to physical and chemical interaction (hydrogen bridges) with the LAA, maintaining it stable in its molecular form.

In addition to a greater number of groups which can interact with the LAA, these groups should present a certain linking intensity (linking power) at the hydrogen bridges about 0.9 of the ratio between the molecular mass of the polymer and the molecular weight of its monomer unit. But in the case of polymers with a molecular mass of about 150,000 g/mol, it is preferable that the amount of heteroatomic groups be equal to the ratio between the molecular mass of the polymer and the molecular weight of its monomer unit. In another example, when the polymer has a molecular mass of about 200,000 g/mol, it is preferable that the amount of heteroatomic groups be equal to 0.9 of the ratio between the molecular mass of the polymer and the molecular weight of its monomer unit.

A polymer that is particularly adequate for the purposes of the present invention is polyvinylalcohol or, less preferably, polyvinylthioalcohol, and in this case the physical and chemical interaction can be represented as follows:

The parameters and conditions for carrying out the process of stabilizing LAA, according to the present invention, will depend upon the hydrogen-bridge-forming compound used and upon the end products that are specifically desired. Such parameters are not, therefore, determinant of the invention and may be easily determined by any person skilled in the art, according to the objectives of each particular situation.

Experiments carried out in accordance with the process of the invention show that it is possible to obtain a greater stability of LAA than 90% for a prolonged period of time and under adverse external conditions. In this way, an amount lower than 10% of subcompounds which could impair the efficiency of resulting aqueous compositions in some way is formed.

Therefore, the invention also provides a stable aqueous LAA composition comprising, in addition to the referred-to ascorbic acid, at least one compound that is linked to the LAA by hydrogen bridges. An aqueous composition with these stability characteristics can show excellent results when used for cosmetic, pharmaceutical or nutritional purposes. It has been found, for instance, that an aqueous composition in accordance with the invention provides surprising results in reducing signs of skin aging, when applied topically. When it is ingested or otherwise administrated for a pharmaceutical purpose, it raises the level of LAA in the organism, which may aim, for instance, at a better synthesis of collagen in the organism, an antiscorbutic action or an antioxidant action and a foreseeable free-radical-destroying action.

For these specific purposes, the aqueous composition of the invention preferably presents a LAA content ranging from about 5 to about 20% m/v, more preferably around 10% m/v, and a content of hydrogen-bridge-forming compound ranging from about 1 to about 5% m/v, preferably around 1% m/v.

The aqueous composition of the invention can also comprise, advantageously, other additives or even other active ingredients which do not interfere in the stability of the LAA, these components depending, of course, on the desired final use for the composition. For instance, it can advantageously include a drinkable carrier which assists in diminishing the solubility of oxygen in the solution by expelling it, thus enhancing the stabilization of the LAA. In the case of a composition for cosmetic or pharmaceutical purpose, for instance, a particularly adequate carrier is a glycol, preferably propyleneglycol, which can be present in a proportion of about 25% v/v, based on the total volume of the composition.

Besides, a composition in accordance with the invention, when formulated as a pharmaceutical composition, can contain other ingredients or compounds having healing properties such as, for example, other vitamins such as vitamin A, B and mineral salts, in addition to ingredients necessary to the metabolism in the case of a composition to be ingested by a human being or an animal. Alternative carriers can include glycerin or vegetable oils. Topical compositions, in turn, may contain hydrating agents, preserving agents, and thickeners such as sodium hyaluronate, nipagin/nipazol and polyacrylates, respectively.

In another aspect of the invention, the association of an aqueous LAA composition, in accordance with the invention, with compounds capable of stimulating the metabolism of the fibroblasts is particularly advantageous, since the latter accent the stimulus to the synthesis of collagen with a view to prevent and correct the skin-supporting structure, thus acting against the wrinkles. An example of such compounds includes retinol and its derivatives, such as retinyl palmitate. The formulations containing a stable aqueous LAA composition together with the compound capable of stimulating the metabolism of the fibroblasts can also be included in a hydrophilic base or in a lipophilic base, or else in an emulsion.

Although some emulsions are capable of enhancing cutaneous irritations when applied topically, such a disadvantage can be minimized or even eliminated by choosing less irritating surfactants and/or by including compounds that attenuate the feeling of irritation.

Anyway, it has been found that the aqueous compositions of the invention, when prepared in the form of a solution, that is to say, with water contents higher than 50% m/v, do not present micelles, the presence of which indicates a form of emulsion. Although it is possible to minimize or eliminate the irritation potential of the topically applicable emulsions, the absence of micelles in the topical aqueous compositions obtained in accordance with the invention can be regarded as an additional advantage, since this eliminates, even more substantially, the irritation resulting from the use.

Another advantage of the stable aqueous compositions of the invention is that the presence of the compound linked to the LAA by hydrogen bridges renders the stability of the composition independent of the definition of a low pH value. In fact, even if the composition reaches higher pH values, for instance, higher than 3.0, a great stability of the LAA is obtained. This characteristic is fundamental to cosmetic or pharmaceutical compositions. Another important advantage, mainly for topical applications, is that the invention provides a favorable permeability of the composition by the corneous extract.

Another advantageous aspect of the invention lies in the ease and economy of the process for preparing such a composition, which dispenses with complex and expensive techniques, since it can be prepared, packed, stored and transported at room temperature and in the presence of oxygen, without losing the stability of the LAA. In a general way, an aqueous composition in accordance with the invention can be prepared by a process which includes the steps of dissolving at least one compound capable of forming hydrogen bridges with the LAA in water, and adding the LAA to the resulting solution.

According to a preferred embodiment of the invention, the aqueous composition is formulated as a stable LAA solution comprising a polymer as described above, linked to the LAA by hydrogen bridges, for example, polyvinylalcohol, and further a drinkable carrier that cosmetically and pharmaceutically acceptable as propyleneglycol. Such a solution may be prepared by a process of preparing a stable LAA solution, characterized by comprising the steps of:

- heating an amount of water;
- adding to this amount of heated water a compound capable of forming hydrogen bridges with LAA in an amount of water ranging from 1 to 5% m/v, and the amount of heated water should be at a temperature capable of promoting the dissolution of the hydrogen-bridge-forming compound, besides simultaneously guaranteeing a substantial elimination of any oxygen present;
- homogenizing the product obtained in (b);
- cooling the resulting product down to a temperature ranging from 10° to 40°;
- adding to the mixture obtained in (d) from 5% to 20% m/v of LAA; and
- homogenizing the resulting solution.

The illustrative examples given below will serve to describe the present invention in a better way. However, the data and procedures illustrated merely refer to some embodiments of the invention and should not be understood as being illustrative of the scope thereof.

In order to prepare all the tests, the LAA (Vitamin C) supplied by ROCHE® in the form of a white powder was used.

EXAMPLE 1

Stability of LAA in an Aqueous Composition in Accordance with the Invention

A solution was prepared which comprised 66.11% of water, 16.53% of propyleneglycol, 16.53% of LAA and 0.83% of polyvinylalcohol (PVA) with the following characteristics:

TABLE I

| Compound | Degree of hydrolisis (%) | Molecular mass (g/mol) | Molecular weight (g/mol) | Amount of monomer units |
|---|---|---|---|---|
| PVA | 88 | 31000 | 44 | 619 |

Figure 2:
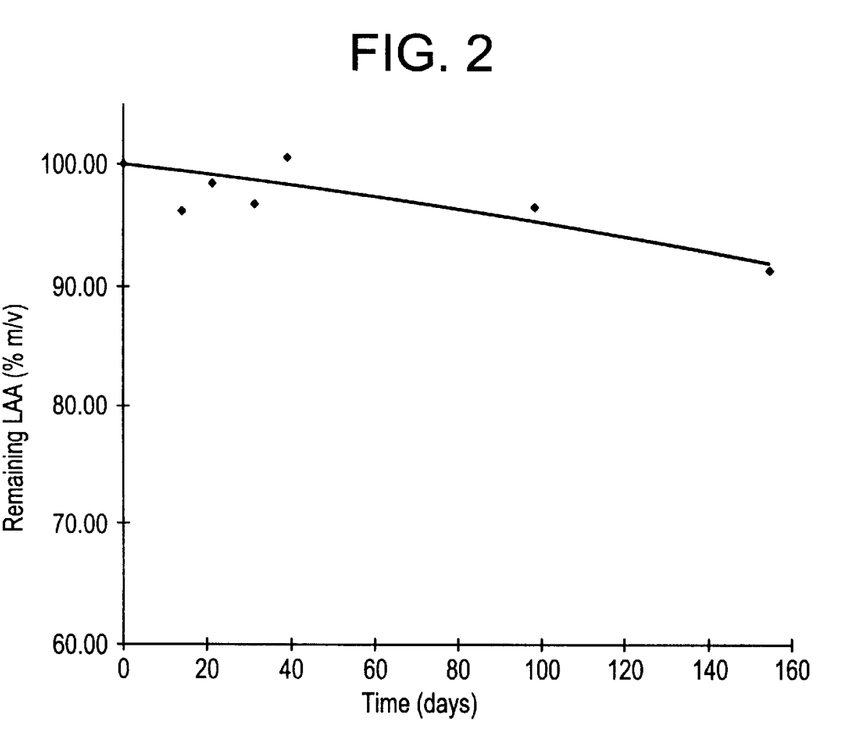
FIG. 2 illustrates the stability of an aqueous LAA composition according to the present invention, when exposed to conditions of room temperature and artificial clarity.

The above composition was subjected to room temperature and artificial clarity, and the data obtained are shown in FIG. 2.

As can be seen from the graph, the LAA contents of the above sample, even after 160 days storage at room temperature and exposed to artificial clarity, present stability higher than 90%.

EXAMPLE 2

Figure 3:
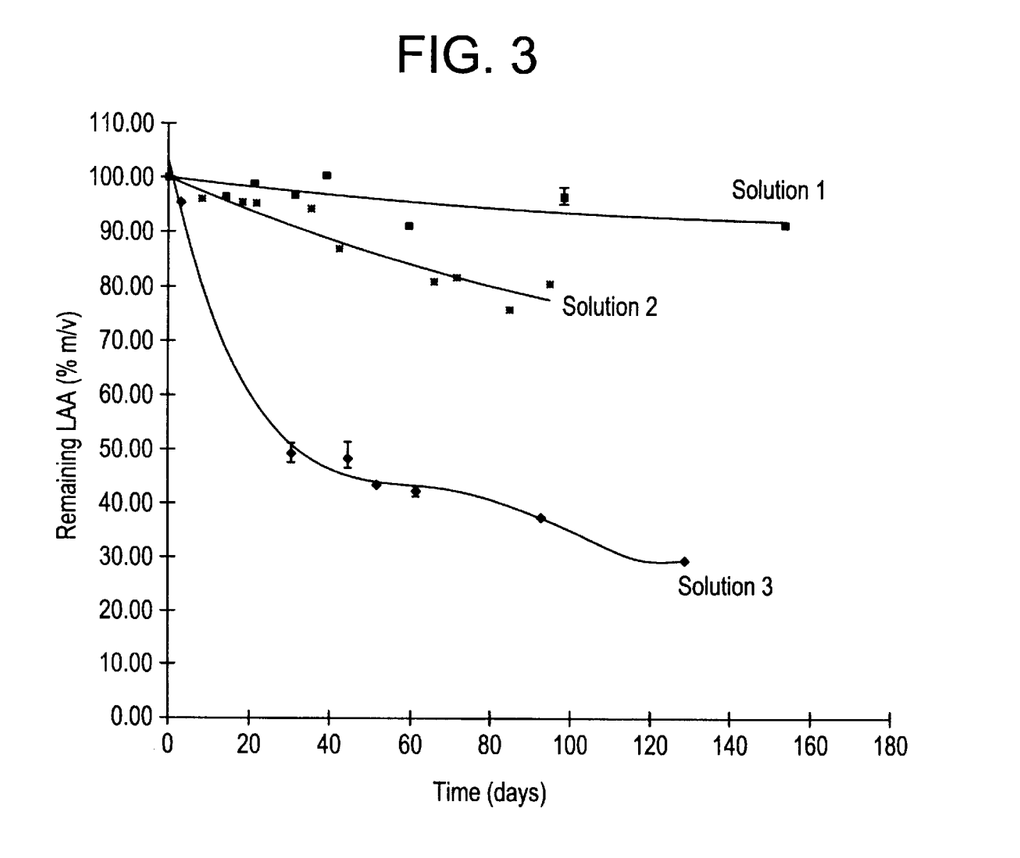
FIGS. 3 and 4 represent graphs comparing the stability of LAA compositions stabilized in according to the present invention and that of other known compositions.

Comparative Example Between a Stable Aqueous Composition in Accordance With the Invention and Other Compositions Proposed for Stabilization of the LAA A solution was prepared in accordance with the invention, comprising 72.79% of water, 17.44% polypropyleneglycol, 9.0 of LAA and 0.9% of the polyvinylalcohol described in example 1, all the concentrations being defined in mass per mass (Solution 1). Additionally a solution was prepared, which comprised the same components and the same proportions as Solution 1, except for the polyvinylalcohol, which was replaced by hydroxyethylcellulose, in the same amount (Solution 2). Also a product available on the market was used (Solution 3), which is a solution presented in the form of a serum containing about 10% of LAA, essences, zinc salts, bioflavoroids, hydrating agent and a preserving agent, and is indicated for topical use with a view to provide a photoprotective effect by virtue of its capacity of controlling the inflammatory response of the skin associated to exposition to sunshine. The three solutions were exposed to artificial clarity at room temperature. The comparative data are presented in FIG. 3, where it can be seen that the stability of Solution 1 (invention) remains above 90%, whereas, to the contrary, there is a drop in the other solutions.

EXAMPLE 3

Comparative Example of the Stability of LAA in Solutions Exposed to Direct UV Radiation Five solutions the ingredients of which are indicated in Table II were compared with each other, solution 1 being a solution in accordance with the invention; solution 2 being analogous to the invention, but replacing the PVA by hydroxyethylcellulose; solutions 3 and 4 being equal to solutions 2 and 1, respectively, but further containing citric acid in order to evaluate the effect of lowering the pH on the stability of the solution. Solution 5 is a product existing on the market, as described in the preceding example (note the description of solution 3 in Example 2).

TABLE II

| Ingredients | Solution 1 | Solution 2 | Solution 3 | Solution 4 | Solution 5 |
|---|---|---|---|---|---|
| water | 20 mL | 20 mL | 20 mL | 20 mL | (*) |
| LAA | 2.5 g | 2.5 g | 2.5 g | 2.5 g | estimated 10% |
| hydroxythylcellulose | 0.25 g | 0.25 g | 0.25 g | 0 | (*) |
| propylenoglycol | 5 mL | 5 mL | 5 mL | 5 mL | (*) |
| citric acid | 0 | 0 | 1.52 g | 1.52 g | (*) |
| PVA | 0.25 g | 0 | 0 | .25 g | (*) |

(*) - unknown.

Figure 4:
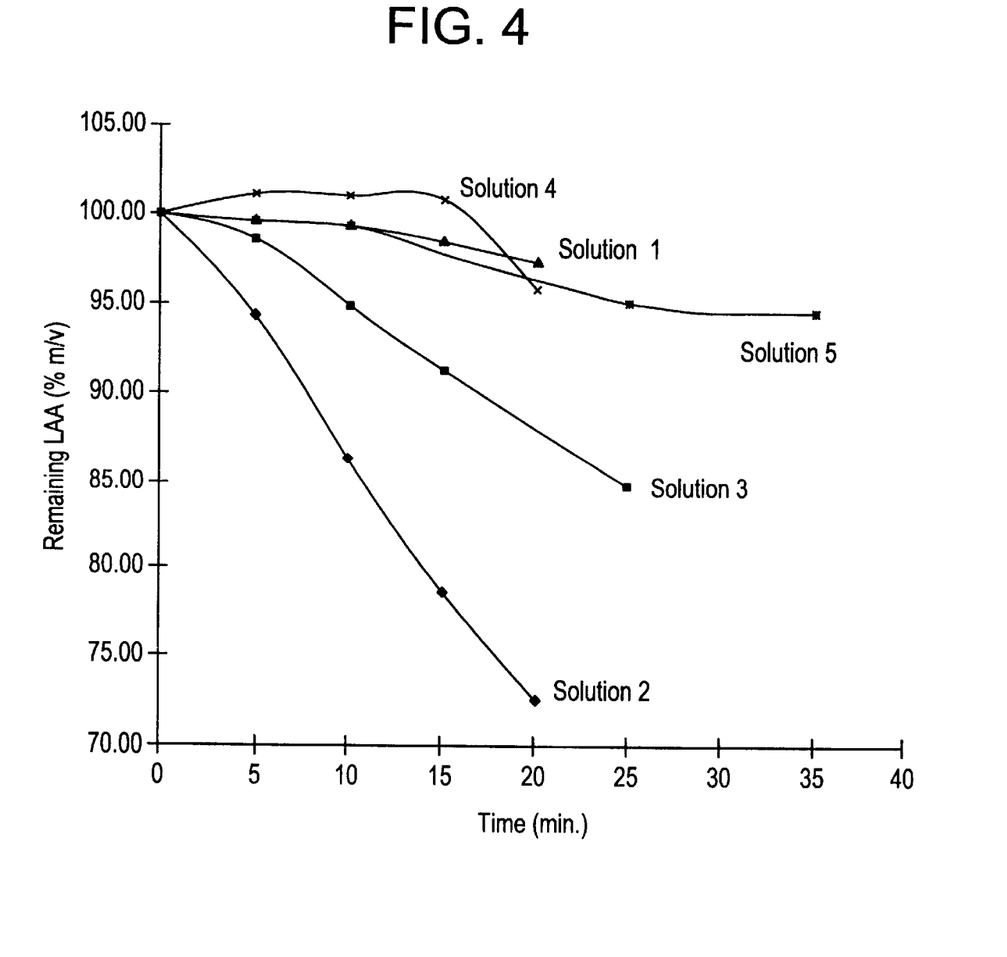

After appropriate dilution for reading in the Spectrophotometer in visible UV, spectra were obtained with determined periods, without removing the cell of sample in the sampling compartment so as to receive visible UV radiation constantly, inducing the degradation of the LAA. FIG. 4 shows the kinetics of degradation of the LAA with the time of exposition to visible UV radiation.

One can note that, in an advantageous and surprising way, the stability of Solution 1 (invention) presents only a slight decrease after 20 minutes' exposition to UV radiation, being also above Solution 5, representative of a market product.

The LAA contents of Solutions 3 and 4, which include citric acid with the function of lowering the respective pH values and thereby maintaining the stability, show that the inclusion of the acid did not fulfil its expected role, there having been a drop in the remaining amount of LAA or loss of stability, whereas Solution 5 presents an acceptable stability under UV radiation.

In a particularly preferred embodiment, a stable aqueous LAA composition as described above is used within organic envelopes permeable to the LAA, which enable its gradual and prolonged release within the organism. The advantage of using such envelopes lies mainly in the fact that they provide additional protection of the aqueous LAA composition against the effects of the environment, besides improving its action in the organism of an individual, especially when it comes to a topical application, because, enabling a prolonged release of the LAA, the envelopes also provide preservation of the target cells, unlike what used to happen with massive doses of LAA, which could cause the death of the referred-to cells.

Envelopes suitable for this purpose are described in U.S. Pat. No. 5,395,620 (Huc et al) and refer to microcapsules containing a cross-linked polymeric wall. For the purposes of the invention these microcapsules are in a substantially globular shape with a statistic size distribution lesser than 800 micra. Preferably, this statistic size distribution is lesser than 100 micra, more preferably from 0.2 to 100 micra, and still more preferably from 3 to 60 micra.

The organic envelopes are advantageously prepared from a matrix containing molecules selected from the group consisting of protein molecules, glucosaminoglycans molecules, polysaccharide molecules and mixtures thereof. The protein molecules and glucosaminoglycan molecules may be of marine origin or may come from land mammals, whereas the useful polysaccharide molecules are of vegetable origin. Preferably, the protein molecules are collagen molecules and the glucosaminoglycan molecules are chondroitin sulphate molecules. But the polysaccharide molecules are preferably galactomannan molecules.

Figure 5:
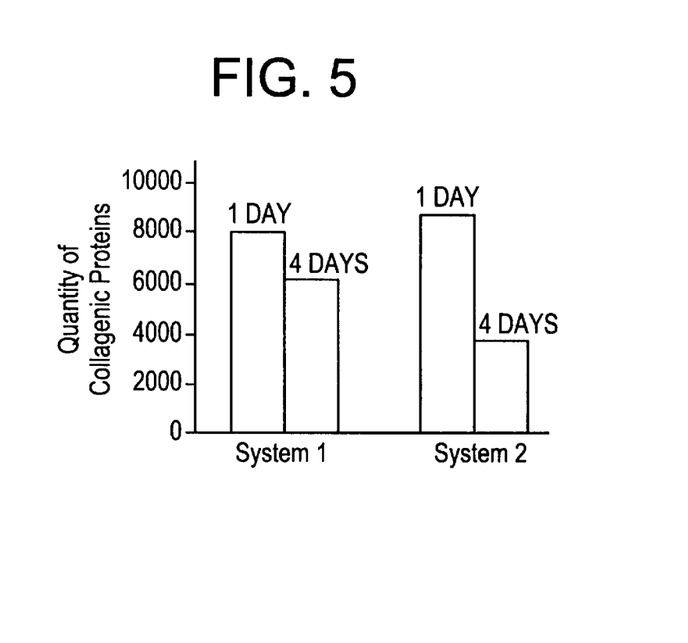
FIG. 5 is a graphical comparison of the quantity of collagenic proteins present for two LAA containing test systems after one and four days.

The tests carried out evidenced the greatest efficiency of the LAA when inserted in the organic envelopes and applied in a monolayer of fibroblasts, as illustrated in the graph of FIG. 5, in which System 1 represents the LAA associated to organic envelopes, whereas System 2 represents the free LAA, without being inserted into the organic envelope.

One can note the maintenance of an intense metabolic activity of production of collagen proteins of the fibroblasts, even after the passage of 4 days.

Figure 6:
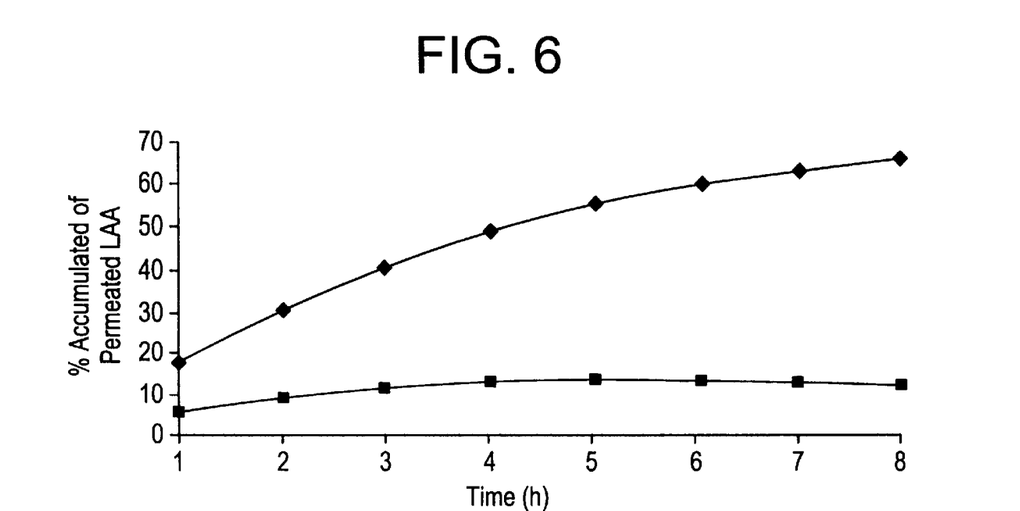
FIG. 6 is a graph illustrating the percent accumulated permeated LAA as a function of time for two test systems.

On the other hand, the fear that the stable aqueous LAA composition in accordance with the invention could not be adequately retained inside said organic envelopes did not prove to be true, since it was found that, surprisingly, stable aqueous LAA compositions including the hydrogen-bridge-forming polymers with a molecular mass as taught herein, that is to say, lesser than from 70,000 g/mol to 200,000 g/mol, drain in a minimum way out of the organic envelopes, as shown by the tests, the result of which is represented by FIG. 6.

As can be seen, an aqueous composition including a polymer with a molecular mass of 67,000 g/mol (indicated by the symbol ♦) is retained in a more advantageous way inside the organic envelopes than in the case of aqueous compositions including a polymer with a molecular mass of 31,000 g/mol (indicated by the symbol ■).

In view of the above considerations about the advantages of associating a stable aqueous LAA composition in accordance with the invention with compounds capable of stimulating the metabolism of the fibroblasts, on the one hand, as well as of the inserting of the aqueous composition into organic envelopes such as those described in U.S. Pat. No. 5,395,620, on the other hand, a specially preferred embodiment of the invention will be represented by a synthesis of these associations, that is to say, an aqueous LAA composition combined with a compound capable of stimulating the metabolism of the fibroblasts and presented inside an organic envelope, as described above.

One should bear in mind that the processes, methods, compositions and products described above merely represent preferred embodiments of the present invention, the scope of which is defined by the accompanying claims.

The Informal Specification filed herewith is incorporated herein by reference.

We claim:

1. A stable levogyre ascorbic acid composition, comprising: levogyre ascorbic acid; at least one compound which is linked to the levogyre ascorbic acid by hydrogen bridges; and a medium containing water.

2. A process according to claim 1, wherein the levogyre ascorbic acid is predominantly dissolved in the medium containing water.

3. A process according to claim 1, wherein said compound capable of forming hydrogen bridges with the levogyre ascorbic acid comprises a plurality of equal monomer units with a molecular weight less than 100 g/mol and with a heteroatomic group in an amount higher than about 70% of a ratio between a molecular mass of said compound and a molecular weight of a monomer unit of the compound.

4. A process according to claim 3, wherein said heteroatomic group is selected from a hydroxyl group or a sulfidric group.

5. A process according to claim 3, wherein the molecular weight of the monomer unit is less than or equal to 60 g/mol.

6. A process according to claim 3, wherein the molecular mass of said compound is less than 70,000, and the amount of heteroatomic groups is about 0.9 of the ratio between the molecular mass of said compound and the molecular weight of the monomer unit.

7. A process according to claim 3, wherein the molecular mass of said compound is about 150,000 g/mol, and the amount of heteroatomic groups is equal to the ratio between the molecular mass of said compound and the molecular weight of the monomer unit.

8. A process according to claim 3, wherein the molecular mass of said compound is about 200,000 g/mol and the amount of heteroatomic groups is equal to 0.9 of the ratio between the molecular mass of said compound and the molecular weight of the monomer unit.

9. A process according to claim 1, wherein said compound capable of forming hydrogen bridges is a polymer.

10. A process according to claim 9, wherein said polymer is polyvinylalcohol.

11. A process according to claim 9, wherein said polymer is polyvinylthioalcohol.

12. A process for producing a stable levogyre ascorbic acid composition according to claim 1, comprising; contacting levogyre ascorbic acid, in a medium containing water, with at least one compound capable of forming hydrogen bridges with the levogyre ascorbic acid.

13. A composition according to claim 12, wherein the levogyre ascorbic acid is predominantly dissolved in said medium containing water.

14. A composition according to claim 12, wherein said compound linked by hydrogen bridges to the levogyre ascorbic acid comprises a plurality of equal monomer units of molecular weight less than 100 g/mol and with a heteroatomic group in an amount higher than about 70% of a ratio between a molecular mass of said compound and a molecular weight of a monomer unit of the compound.

15. A composition according to claim 14, wherein said heteroatomic group is selected from a hydroxyl group or a sulfidric group.

16. A composition according to claim 14, wherein the molecular weight of the monomer unit of said compound is less than or equal to 60 g/mol.

17. A composition according to claim 14, wherein the molecular mass of said compound is less than 70,000, and the amount of heteroatomic groups is about 0.9 of the ratio between the molecular mass of said compound and the molecular weight of the monomer unit.

18. A composition according to claim 14, wherein the molecular mass of said compound is about 150,000 g/mol, and the amount of heteroatomic groups is equal to the ratio between the molecular mass of said compound and the molecular weight of the monomer unit.

19. A composition according to claim 14, wherein the molecular mass of said compound is about 200,000 g/mol, and the amount of heteroatomic groups is equal to 0.9 of the ratio between the molecular mass of said compound and the molecular weight of the monomer unit.

20. A composition according to claim 12, wherein the composition comprises from about 5 to about 20% m/v of levogyre ascorbic acid and from about 1 to 5% m/v of the compound linked to the levogyre ascorbic acid by hydrogen bridges, based on the total composition.

21. A composition according to claim 20, wherein the composition comprises about 10% m/v of levogyre ascorbic acid and about 1% m/v of the compound linked to the levogyre ascorbic acid by hydrogen bridges, based on the total composition.

22. A composition according to claim 12, wherein said compound capable of forming hydrogen bridges is a polymer.

23. A composition according to claim 22, wherein said polymer is polyvinylalcohol.

24. A composition according to claim 22, wherein said polymer is polyvinylthioalcohol.

25. A composition according to claim 12, further comprising a drinkable carrier.

26. A composition according to claim 25, wherein said drinkable carrier is a glycol.

27. A composition according to claim 26, wherein said glycol is propyleneglycol.

28. A composition according to claim 25, wherein the carrier is present in a proportion of about 25% v/v, based on a total volume of the composition.

29. A composition according to claim 12, wherein the composition is a cosmetic composition.

30. A composition according to claim 12, wherein the composition is a pharmaceutical composition.

31. A composition according to claim 12, wherein the composition is a nutritional composition.

32. A composition according to claim 29, wherein the cosmetic composition is a topical solution.

33. A composition according to claim 32, wherein the topical solution diminishes skin signs.

34. A composition according to claim 12, further comprising at least one compound capable of stimulating metabolism of fibroblasts.

35. A composition according to claim 34, wherein said compound capable of stimulating the metabolism of fibroblasts is retinol.

36. A composition according to claim 34, wherein said compound capable of stimulating the metabolism of fibroblasts is a derivative of retinol.

37. A composition according to claim 36, wherein said compound capable of stimulating the metabolism of fibroblasts is retinyl palmitate.

38. A composition according to claim 34, further comprising a hydrophilic base.

39. A composition according to claim 34, further comprising a lipophilic base.

40. An emulsion having an aqueous phase, including levogyre ascorbic acid and at least one compound linked to the levogyre ascorbic acid by hydrogen bridges.

41. A process for preparing a stable levogyre ascorbic acid composition according to claim 12, comprising:

(a) heating an amount of water;

(b) adding to this amount of heated water a compound capable of forming hydrogen bridges with levogyre ascorbic acid, wherein the compound capable of forming hydrogen bridges is added in an amount ranging from 1 to 5% m/v, and wherein said amount of heated water is at a temperature capable of promoting dissolution of the compound capable of forming hydrogen bridges while simultaneously substantially eliminating any oxygen present, to thereby produce a first product;

(c) homogenizing the first product obtained from step (b) to thereby produce a second product;

(d) cooling the second product to a temperature ranging from 10° C. to 40° C. to thereby produce a third product;

(e) adding to the third product obtained from step (d) from 5% to 20% m/v of levogyre ascorbic acid to thereby produce a solution; and (f) homogenizing the solution.

42. A process according to claim 41, further comprising including with the amount of water a drinkable carrier, prior to said heating.

43. A process according to claim 41, wherein, during said heating, the temperature is lower than 100° C.; and wherein the levogyre ascorbic acid is predominantly dissolved in water.

44. A process according to claim 43, wherein said temperature during the heating ranges from about 30° C. to below 100° C.

45. A process according to claim 43, wherein said temperature during the heating ranges from about 67° C. to about 97° C.

46. A process according to claim 41, wherein said compound capable of forming hydrogen bridges is a polymer.

47. A process according to claim 46, wherein said polymer is polyvinylalcohol.

48. A process according to claim 46, wherein said polymer is polyvinylthioalcohol.

49. A process according to claim 42, wherein said drinkable carrier is a glycol.

50. A process according to claim 49, wherein said glycol is propyleneglycol.

51. A method for cosmetic, pharmaceutic or nutritional treatment comprising: administering to an individual in need of such a treatment an aqueous levogyre ascorbic acid composition as defined in claim 12.

52. A method according to claim 51, wherein said composition is administered topically.

53. A method according to claim 52, wherein the treatment is a cosmetic treatment for eliminating skin signs.

54. A method according to claim 51, wherein the composition is administered orally.

55. A method according to claim 54, wherein the treatment is a nutritional treatment for raising a level of levogyre ascorbic acid in the individual.

56. A method according to claim 51, wherein the composition is administered intravascularly.

57. A method according to claim 56, wherein the treatment is a pharmaceutical treatment for raising a level of levogyre ascorbic acid in a blood current of the individual.

* * * * *

UNITED STATES PATENT AND TRADEMARK OFFICE
CERTIFICATE OF CORRECTION

PATENT NO. : 6,037,481
DATED : April 18, 2003
INVENTOR(S) : Roberto Alcantara Martins Zucchetti et al.

It is certified that error appears in the above-identified patent and that said Letters Patent is hereby corrected as shown below:

Column 16,
Lines 58 and 61, change "according to claim 1" to -- according to claim 12 --.

Column 17,
Line 21, change "according to claim 1" to -- according to claim 12 --.
Lines 32, 35 and 63, change "according to claim 12" to -- according to claim 1 --.

Column 18,
Lines 6, 13, 22, 24, 26, 32 and 51, change "according to claim 12" to -- according to claim 1 --.

Column 20,
Line 5, change "according to claim 12" to -- according to claim 1 --.

Signed and Sealed this

Nineteenth Day of August, 2003

JAMES E. ROGAN
*Director of the United States Patent and Trademark Office*